(12) United States Patent
Johnsen

(10) Patent No.: US 9,116,053 B2
(45) Date of Patent: Aug. 25, 2015

(54) SYSTEM FOR MEASUREMENT WITH PEARLS

(76) Inventor: Asle Johnsen, Tønsberg (NO)

( * ) Notice: Subject to any disclaimer, the term of this patent is extended or adjusted under 35 U.S.C. 154(b) by 585 days.

(21) Appl. No.: 13/201,096

(22) PCT Filed: Feb. 12, 2010

(86) PCT No.: PCT/NO2010/000054
§ 371 (c)(1),
(2), (4) Date: Aug. 11, 2011

(87) PCT Pub. No.: WO2010/093258
PCT Pub. Date: Aug. 19, 2010

(65) Prior Publication Data
US 2011/0309844 A1    Dec. 22, 2011

(30) Foreign Application Priority Data
Feb. 13, 2009   (NO) .................................. 2009 0716

(51) Int. Cl.
*G01R 27/04* (2006.01)
*G01R 27/00* (2006.01)
*G01K 5/72* (2006.01)
*G01N 22/00* (2006.01)
*G01D 1/00* (2006.01)
*G01D 15/00* (2006.01)
*G01D 21/00* (2006.01)
*G01K 3/00* (2006.01)
*G01K 5/48* (2006.01)
*G01R 31/08* (2006.01)
*G01R 27/02* (2006.01)
*G01K 3/14* (2006.01)
*G01K 7/16* (2006.01)

(52) U.S. Cl.
CPC .. *G01K 5/72* (2013.01); *G01D 1/00* (2013.01); *G01D 15/00* (2013.01); *G01D 21/00* (2013.01); *G01K 3/005* (2013.01); *G01K 5/48* (2013.01); *G01K 5/486* (2013.01); *G01N 22/00* (2013.01); *G01K 2003/145* (2013.01); *G01K 2007/166* (2013.01); *G01R 27/02* (2013.01); *G01R 31/08* (2013.01)

(58) Field of Classification Search
CPC .................. G01K 2003/145; G01K 2007/166; G01K 5/48; G01K 5/486; G01K 5/72; G01R 31/08; G01R 27/02
USPC ......................................... 324/642, 637, 600
See application file for complete search history.

(56) References Cited

U.S. PATENT DOCUMENTS

| 2,753,548 A | | 7/1956 | Gates |
| 3,510,762 A | | 5/1970 | Leslie |
| 3,938,385 A | | 2/1976 | Horwath |
| 4,023,412 A | * | 5/1977 | Luke et al. ............... 374/177 |
| 4,878,226 A | * | 10/1989 | McQuoid et al. ............ 374/166 |
| 5,179,342 A | | 1/1993 | Wolfe et al. |
| 5,185,594 A | | 2/1993 | DeChurch |
| 5,648,724 A | * | 7/1997 | Yankielun et al. ............ 324/533 |
| 2009/0074348 A1 | * | 3/2009 | Xia et al. ...................... 385/12 |

FOREIGN PATENT DOCUMENTS

| GB | 1 465 515 A | 2/1977 |
| JP | 9-060899 A | 3/1997 |

* cited by examiner

*Primary Examiner* — Amy He
(74) *Attorney, Agent, or Firm* — Birch, Stewart, Kolasch & Birch, LLP

(57) ABSTRACT

A system is provided for measurement with one or more sensors including at least one signal conductor and at least one pearl, wherein the pearl a device configured to change an impedance mismatch with an external environmental effect.

6 Claims, 2 Drawing Sheets

SYSTEM FOR MEASUREMENT WITH PEARLS

BACKGROUND OF THE INVENTION

1. Technical Field

The invention regards a measurement system in general and particularly a system for measurement using one or more sensors.

2. Background Art

There is a need to measure temperatures across large areas, particularly temperatures where a heating cable is deployed. Even though an average temperature is within acceptable range values, local areas with harmful temperature can occur. This can typically be found where clothes or thick carpets are placed upon a floor heated by heating cables. Typical forms for damages are damages on heating cable or damages on the flooring material.

From the known art one should refer to heating cable with negative thermal coefficient, that is heating cables with a resistance that is changed relating to the temperature of the heating cable in such a way that an increase in a temperature of the heating cable with result in a reduction in the power of the heating cable. This system functions where the temperature is even, however small localised areas with increased temperature will not be compensated sufficiently, a problem that arises for instance on bathroom floors where a thick towel is placed on the floor. The temperature can then increase so far that the heating cable will be damaged or will be subjected to a reduced lifetime.

One should also refer to distributed systems where small sensors attached to the heating cable measure the temperature and communicates across a data network typically in a form of serial communication. This overcomes the above mentioned problems; on the other hand the complexity and costs are significant. First of all this means that electronics is needed at every single measurement point and also at least 2 conductors are needed for communication, typically ground and signal overlaid a power supply for each measurement point. If one measurement point is rendered inoperable, there is a risk that the communication between sensors will become partly or fully out of operations. If ground connector or signal connector is damaged all measurement points could be put out of operation.

There is therefore a need for a product that overcomes the above mentioned problems.

THE OBJECTIVE OF THE INVENTION

The objective of the invention is to provide a system for measurement with one or more sensors, typically related to heating cables. It is desirable that the sensors are simple in production and reliable in use.

SUMMARY OF THE INVENTION

With this invention a system is thus provided for measurement with one or more sensors wherein a system for measurement using one or more sensors comprises at least one signal conductor and at least one pearl, wherein said pearl comprises means for changing an impedance mismatch due to external environmental effect. Useful and preferred embodiments of the invention are disclosed in the dependent claims.

According to the present invention one or more measurement units, herein denoted pearls, are provided by or preferably around a conductor, typically a heating cable. Each pearl comprises an isolator nearest the conductor, wherein said isolator has preferable a high thermal coefficient of expansion. Outside the isolator on the other side of the conductor an electrical connecting material is provided called reflector.

Means for Solving the Problems

The present invention achieves the objectives disclosed above using a system for measurements using one or more sensors.

More specifically this is achieved by providing a system comprising at least one signalling conductor and at least one pearl comprising an isolator and a means for changing an impedance mismatch varying with an external environmental influence, typically temperature. This means is typically an isolator with a high positive or negative thermal coefficient of expansion, however also other means are possible such as structures used in thermostats in the form of bimetallic arm.

The following reference numbers and signs refer to the drawings:

| | |
|---|---|
| 10 | Measurement system |
| 11 | Heating cable |
| 20 | Pearl |
| 21 | Through-feed |
| 22 | Isolator |
| 23 | Reflector |
| 24 | Casing |
| 25 | Bimetallic arm |
| 26 | Extreme point for a bimetallic arm |
| 27 | Receiver |
| 30 | Control unit |
| 31 | Power control unit |
| 32 | Signal generator |
| 33 | Reflex measurement unit |
| 34 | Coupling unit |

Terminology

A first order reflected signal is a signal that is reflected from one pearl subjected to an emitted signal.

A second order reflected signal is a signal that is reflected from a pearl which is subjected to a first order reflected signal.

DETAILED DESCRIPTION

The basic principle of the invention is that a conducting object near a signal conductor changes the impedance locally in the signal conductor. Where the signal conductor otherwise is uniform the locally changed impedance will effectively be an impedance mismatch which in turn gives a rise to a reflection for a signal passing through the signal conductor. The degree of reflection is dependent on impedance mismatch which in turn is dependent on the size of the conducting object and the distance between the conducting object and the signal conductor.

The inventor has found that providing a measurement unit in the form of a conducting device, typically in the form of a casing separated by an isolator with preferably a large thermal coefficient of expansion from a signal conductor, measurement of reflections of signals emitted to the signal conductor will give a temperature indication for area near the casing and the isolator. Since the distance between transmitter and the receiver of the signals on the one hand and the measurement unit on the other hand are related to half the signal velocity of the signal conductor and the time delay between emission and reception of the signal, this means that one can provide a plurality of measurement points along the signal conductor and separate the reflections from each measurement point from each other. This can beneficially be combined with a heating cable as a signal conductor where the measurement points will be able to warn of too high temperature along the cable.

The invention will be disclosed in details with reference to the drawings showing several embodiments.

Preferred Embodiment

Figure 1:
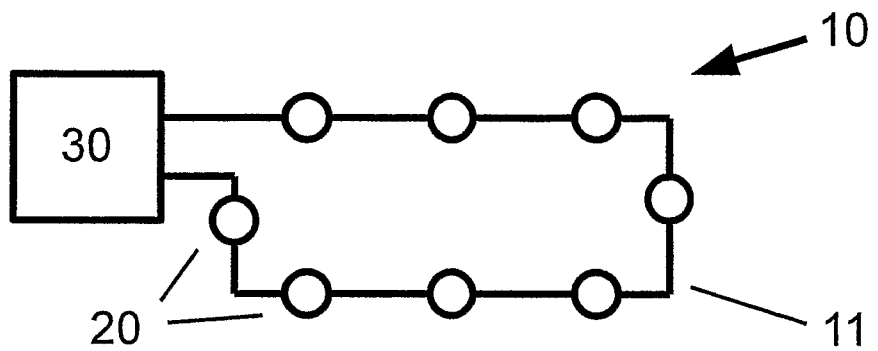
FIG. 1 shows an overview of a typical embodiment of the invention.

FIG. 1 shows schematically an overview of a typical embodiment of the invention where a measurement system 10 comprises a heating cable 11 attached to at least one measurement unit called pearl 20. A control unit 30 is connected to the heating cable 11 and applies power on this for heating. The control unit also emits pulses or high frequency signals and measures the reflections from the at least one pearl 20 in order to monitor the temperature of the at least one pearl and reduce the applied effect if the temperature exceeds a defined upper temperature. The heating cable thus also operates as a signal conductor.

Figure 2A:
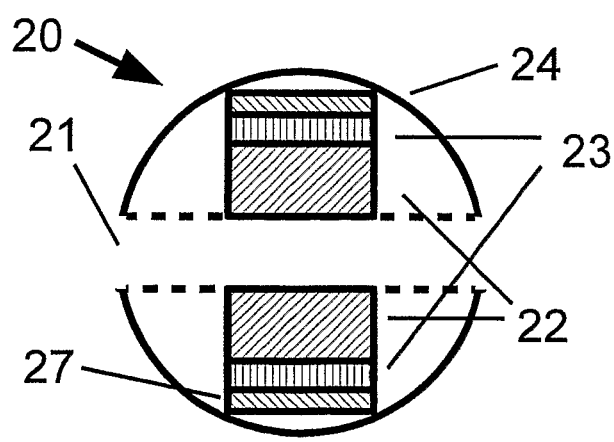
FIG. 2a shows the structure of a pearl in a preferred embodiment.

FIG. 2a shows schematically the structure of a pearl 20 in a preferred embodiment, comprising through-feed 21 for a signal conductor, typically in the form of a heating cable 11.

Outside the through-feed 21 is an isolator 22 provided. It is an advantage that the isolator 22 is positioned close and uniformly around the heating cable 11 in such a way that the reflections occur in an interval common for all pearls in such a way that one achieves good resolution for a common amplification of the reflections. It is also an advantage that the isolator has sufficient mechanical stability in such a way that parameters do not change over time or when the heating cable is positioned into concrete for instance underneath a bathroom floor. At the same time it is an advantage that the isolator is selected for a high thermal coefficient of expansion, positive or negative, in such a way that the changes in impedance is sufficiently large to be measureable.

Outside the isolator 22 a reflector 23 is provided, a conducting object giving rise to an impedance mismatch for the signal conductor. The reflector must be sufficiently malleable in such a way that it remains conformal with the isolator when this expands. This can be achieved either by using a soft material, optionally a material which is cut into a shape giving it a spring action.

Outside the reflector 23 a casing 24 is provided, the purpose being to protect the pearl against unintentional mechanical stress as well as preventing entry of moisture which could cause significant absorption and thus attenuation of signal as well as reflected signal. During production it is therefore an advantage that the cable is produced in a way that protects the pearls against unintentional moisture intrusion.

Figure 3:
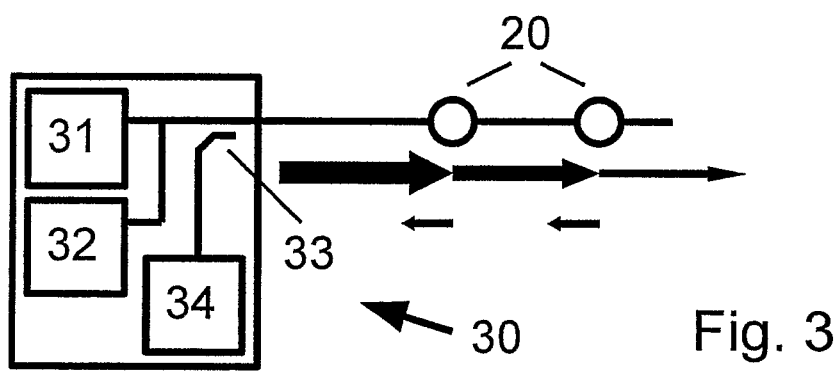
FIG. 3 shows the path of the signal in an embodiment using a plurality of pearls on one heating cable.

FIG. 3 shows the signal path in an embodiment with a plurality of pearls on one heating cable. Signal generator 32 emits a signal into the cable, said signal being super-positioned onto the applied power. A reflection of the signal occurs in a pearl 20 and a reflected signal is emitted from the pearl in opposite direction of the signal. A reduced signal continuous further and a new reflection takes place in the next pearl. For each emitted signal a set of reflected signals arises and are received by a reflection measurement unit through a coupling unit 34, typically in the form of a directive signal coupling unit as known from RF-technique.

It is desirable that the reflection is small compared to the signal which arrives into a pearl. In the following it is for simplicity assumed a reflection of 1 percent and that absorptions are insignificant.

First of all this means that the emitted signal will propagate along the signal conductor with little loss. First pearl is applied a signal of 100 percent of the emitted signal, while subsequent pearl is applied a signal corresponding to 99 percent of the applied signal. This means also that the first reflected signal of the reflected signal of the emitted signal, here called the second order reflected signal, is 1 percent of a percent. This corresponds to 1-2 bit in a 8 bits analog digital converter, here called ADC, the full dynamic range corresponding to the signal for the first reflection from the first pearl. If the second ordered reflected signal and thus also higher order reflected signals are regarded as insignificant compared to the reflected signal of the emitted signal, the signal applied to a pearl can then be simplified to $$S_p = S_0(1-r)\hat{0}p$$

wherein $S_p$=the signal applied to pearl number p counted from the signal generator where p=0 is the first pearl $S_0$=the signal emitted from the signal generator and applied to pearl 0, which is the first pearl r=coefficient of reflection, here set to 1 percent p=index for pearl where p=0 is the first pearl, that this is the first pearl counted from the signal generator Assuming that r=1 percent this means that the signal $S_{100}$ received in pearl 100 is approximately 36 percent, that is the reflection is approximately 36 percent of the reflection from the first pearl. This reflection will be attenuated on its way back to the reflex measurement unit down to the square of this that is approximately 13 percent of the reflection from the first pearl. This is still a higher level than noise from second order reflected signals.

Secondly a low degree of reflection means that a first ordered reflected signals propagates with insignificant loss and that second and higher ordered reflected signals, which is noise in terms of measurement, are insignificant.

Since $S_0$ is significantly larger than the reflection from $S_1$, it is desirable to separate the signals in such a way that the signal generator 32 is not overloading the reflex measurement unit 33. This is preferably achieved using a directive coupling unit.

The reflex measurement unit thus redundantly measure a first ordered reflected signal from each pearl, the signal time separation is related to the spatial separation along the signal conductor. During calibration, where all pearls are kept at the known temperature, the reflex measurement unit will measure the reflection from the pearls. If one reflection is above or below a given threshold, the effect applied to the power cable will be reduced in such a way to protect against overheating.

The signal applied to the signal conductor can be discrete pulses as well as a radio frequency signal. Discrete pulses are technically simple to create as well as measure, though the disadvantage is that the signal energy is limited. By instead using a sweeping radio frequency signal and mix the applied signal together with the received reflected signal a number of peaks in a radio frequency diagram will be obtained, each peak representing a pearl. Even though this increases the complexity significantly a larger energy will on the other hand be provided for more advanced method for signal processing as known to those skilled in the art in signal processing as well as forms for Fourier transforms and averaging.

The signal conductor can be equipped with a terminator to prevent strong reflections from the end of the signal conductor. This can be done as known from for instance high speed data buses such as SCSI.

Variations in Embodiment

A number of variations of the above can be envisaged that nevertheless falls in under the main principles of the invention.

Figure 2B:
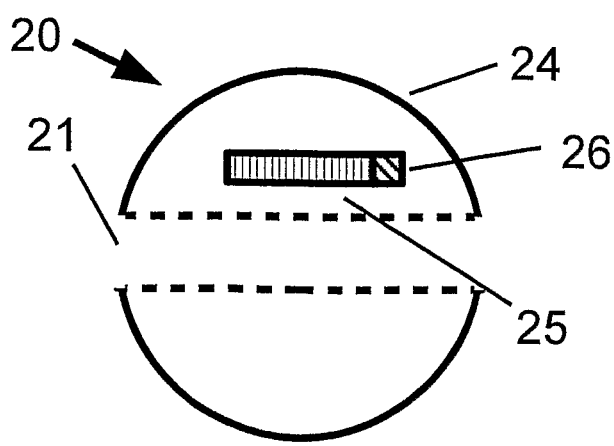
FIG. 2b shows the structure of a pearl in an alternative embodiment where a bimetallic arm changes the amplitude of a reflected signal.
Figure 2C:
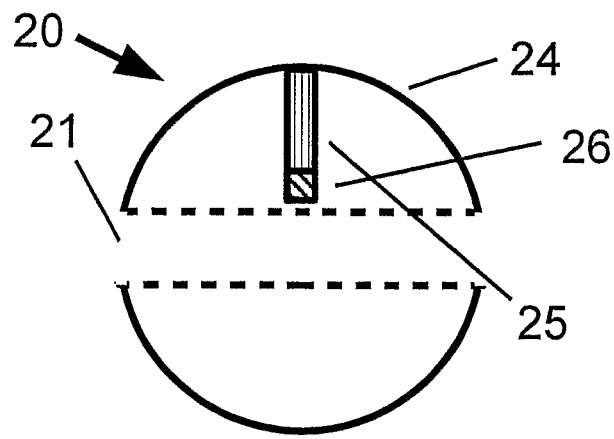
FIG. 2c shows the structure of a pearl in an alternative embodiment where a bimetallic arm changes the phase for a reflected signal.

In the preferred embodiment an isolator is used with defined thermal coefficient of expansion in order to change an impedance mismatch. One can imaging that this isolator is replaced with a bimetallic arm 25 as known from thermostats, wherein the extreme point of the arm 26 various a distance to the signal conductor based on the temperature of the arm as shown in FIG. 2b. The arm can also be provided using non-metallic parts such as plastic of different thermal coefficients of expansion. Alternatively the extreme point 26 of the arm 25 can move along the signal conductor and thereby modulate phase instead of amplitude for the reflected signal, as shown in FIG. 2c. With the increased complexity that this entails one will on the other hand achieve a large change in the reflected signal.

The bimetallic structure can be provided as a micro-electro-mechanical system (MEMS) fabricated using typical semiconductor-conductor processes in for instance silicon. An embodiment as MEMS gives a rise to further possibilities for integrating a filter enabling the pearl to give a response on a predetermined frequency band. Such a system can be attached to the heating cable using direct electrical connection, frequently known as vampire connector. This gives a rise to a large degree of uniformity in production, simple attachment during production and due to the small distances also a possibility for high sensitivity due to large variations in the coefficient of reflection with changes in temperature.

Even though the isolator used in the preferred embodiment is based on a thermal expansion coefficient one can also imaging the use of a material having a phase transition in the temperature interval to be monitored.

It can also be an advantage to provide the pearl with a material of a thermal coefficient of expansion, here known as receiver, with opposite sign of the isolator 22 and thus maintain the volume of the pearl 20 nearly constant.

One can also imaging that the isolator is changing properties based not on temperature but also on pressure, deformation or chemical action such as moisture. Chemical effect can be made selective in that the through-feed 21 is made permeable for specific chemical material and that the isolator 22 for instance swells by absorption or reaction with the chemical effect.

One can also use pearls of different kinds in the same system.

Figure 4:
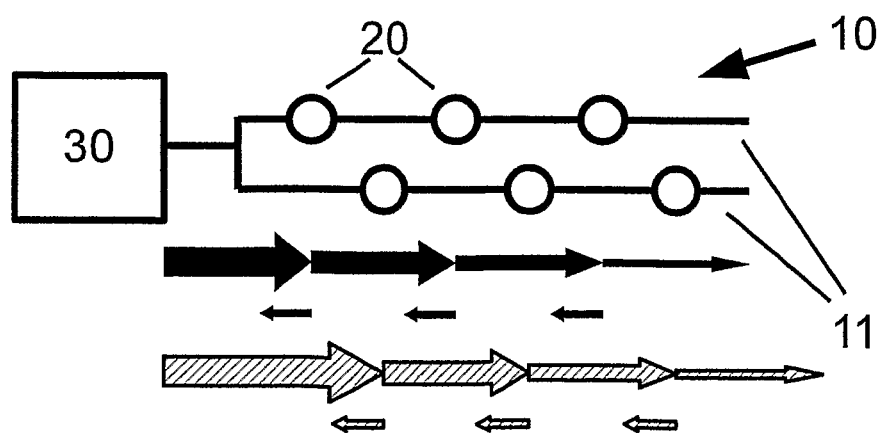
FIG. 4 shows the path of the signal in an embodiment with a plurality of pearls on two attached heating cable.

The system can also be used with a plurality of connected signal conductors in which case it is an advantage that the pearls are positioned in such a way that the first ordered reflected signals do not overlap to such a degree that these cannot be resolved. This is shown in FIG. 4 where 2 connected signal conductors are used. The signal path of the upper signal conductor 11 is indicated using solid arrows where the signal path in the lower signal conductor 11 is indicated by hatched arrows. As shown a positioned offset between the signal conductors 11 will result in that the reflected signals, here indicated by arrows pointing towards left are easily resolved in time and thus enable identification of what reflected signal belonging to what signal conductor.

By using pearls with different frequency response one can use even more connected signal conductors without overlap of first ordered reflected signals.

INDUSTRIAL APPLICABILITY

The invention is useful for distributed measurement systems that are where one desires to make measurements across a plurality of local areas. The present invention provides a number of advantages over the known art:

the pearls are simple in structure, manufacturing and positioning the pearls do not require local power supply, instead use the energy of the signal in the signal conductor, thus reducing the need for extra signal conductor one defect pearl does not necessarily destroy the measurements from other pearls, neither before nor behind as seen from the signal generator 32 missing or incorrectly positioned pearls will not destroy functionality in the system other by not giving a measurement result from the area where the pearl should have been positioned.

Thus the system is useful for areas where high reliability is required.

The invention claimed is:

1. A system for measurement with at least one pearl, comprising:
    at least one signal conductor; and
    a plurality of pearls, wherein each of said plurality of pearls comprises a device configured to change an impedance mismatch with an external environmental effect, the device comprising a reflector; and an isolator with a thermal coefficient of expansion,
    wherein the device is configured in a manner such that the external environment effect changes a size of the isolator, which in turn changes at least one of a size of the reflector and a distance between the reflector and the at least one signal conductor, giving rise to a change in impedance mismatch which in turn changes degree of reflection, and
    wherein said plurality of pearls are separately arranged along the at least one signal conductor, and each of the plurality of pearls is independent of each other.

2. The system according to claim 1, wherein the reflector is provided outside the isolator.

3. The system according to claim 1, wherein the device configured to change an impedance mismatch comprises:
    a bimetallic arm comprising an extremity,
    wherein a temperature change moves the extremity with respect to the conductor.

4. The system according to claim 1, wherein the change in impedance mismatch substantially relies on the dimensional change of at least one of the size of the reflector and the distance between the reflector and the at least one signal conductor.

5. A method for measurement with a plurality of pearls, comprising:
    emission of an emitted signal from a signal generator on a signal conductor; and reception by a reflex measurement unit of at least one first ordered reflected signal, reflected by a first pearl of said plurality of pearls applied with the emitted signal, wherein each of said plurality of pearls comprises a device configured to change an impedance mismatch with an external environmental effect, the device comprising a reflector; and an isolator with a thermal coefficient of expansion, wherein the device is configured in a manner such that the external environmental effect changes a size of the isolator, which in turn changes at least one of a size of the reflector and a distance between the reflector and the signal conductor, giving rise to a change in impedance mismatch which in turn changes degree of reflection, and wherein said plurality of pearls are separately arranged along the at least one signal conductor, and each of the plurality of pearls is independent of each other.

6. The method according to claim 5, wherein the change in impedance mismatch substantially relies on the dimensional change of at least one of the size of the reflector and the distance between the reflector and the signal conductor.

\* \* \* \* \*